(12) United States Patent
Ng

(10) Patent No.: US 6,589,150 B1
(45) Date of Patent: Jul. 8, 2003

(54) APPARATUS AND METHOD TO FOLD AND SECURE SANITARY NAPKIN FLAPS PRIOR TO PACKAGING

(75) Inventor: Tony Ng, East Brunswick, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 361 days.

(21) Appl. No.: 09/655,457

(22) Filed: Sep. 5, 2000

(51) Int. Cl.⁷ ................................................ B31F 1/00
(52) U.S. Cl. ...................... 493/423; 493/429; 493/441; 156/227
(58) Field of Search ................................ 493/231, 244, 493/405, 423, 425, 426, 441, 429, 442; 156/227, 256, 264, 226

(56) References Cited

U.S. PATENT DOCUMENTS

| 4,285,343 A | 8/1981 | McNair | 128/287 |
| 4,589,876 A | 5/1986 | Van Tilburg | 604/385 R |
| 4,648,861 A * | 3/1987 | Pierce | 493/333 |
| 4,687,478 A | 8/1987 | Van Tilburg | 604/387 |
| 4,701,178 A | 10/1987 | Glaug et al. | 604/387 |
| 4,759,754 A | 7/1988 | Korpman | 604/387 |
| 4,938,739 A * | 7/1990 | Nilsson | 493/422 |
| 4,979,932 A * | 12/1990 | Burnside | 493/134 |
| 4,995,600 A * | 2/1991 | Kovac et al. | 270/45 |
| 5,176,615 A * | 1/1993 | Munsch | 493/427 |
| 5,662,639 A | 9/1997 | Tanaka et al. | 604/387 |
| 5,800,654 A | 9/1998 | Davis et al. | 156/227 |
| 5,964,689 A * | 10/1999 | McFall et al. | 493/395 |
| 6,458,066 B1 * | 10/2002 | Breton et al. | 493/423 |

FOREIGN PATENT DOCUMENTS

| EP | 0 347 319 B1 | 1/1993 | A61F/13/15 |
| WO | WO 88/04546 | 6/1988 | A61F/13/16 |

* cited by examiner

Primary Examiner—Eugene Kim

(57) ABSTRACT

The present invention is directed to a sanitary napkin having flaps folded onto the main body of the napkin and temporarily held in this position by a finger means. At least one end of the napkin is then folded onto the flaps thereby retaining the flaps in their folded position. The finger means is then disengaged from contact with the napkin.

13 Claims, 4 Drawing Sheets

APPARATUS AND METHOD TO FOLD AND SECURE SANITARY NAPKIN FLAPS PRIOR TO PACKAGING

FIELD OF THE INVENTION

This invention is directed to sanitary napkins having flaps. More particularly, this invention is directed to an efficient apparatus and method of folding and securing these flaps during the process of making sanitary napkins.

BACKGROUND OF THE INVENTION

Sanitary napkins having flaps extending outwardly from the longitudinal side margins are well known in the art. For example, U.S. Pat. No. 4,589,876 issued May 20, 1986, to Van Tilburg and U.S. Pat. No. 4,687,478 issued Aug. 18, 1987, to Van Tilburg disclose preferred sanitary napkins with flaps and are incorporated herein by reference to illustrate flapped sanitary napkin constructions.

It is also well known in the art to fold the flaps to overlay the main body of the pad during the manufacturing process. For example, in U.S. Pat. No. 4,759,754 to Korpman, an adhesive tab is used for maintaining the flaps in the desired disposition overlaying the backsheet during packaging. U.S. Pat. No. 4,701,178 issued Oct. 20, 1987, to Glaug et al. discloses a sanitary napkin having a single release strip which covers the centrally located adhesive of the backsheet and over which release strip the flaps are folded.

Alternative means for maintaining the flaps in a folded disposition prior to first use of the sanitary napkin by the wearer are shown for example, in U.S. Pat. No. 4,285,343 to McNair which discloses a sanitary napkin with flaps (side panels) that are folded over the upper surface of the central absorbent element for packaging. At the time of the first use by the wearer, the flaps are usually unfolded to facilitate installation of the sanitary napkin into the wearer's undergarment. Adhesive patches on a garment facing surface of the flaps are covered with individual strips of release paper.

An alternative method of holding the flaps in place is to utilize the release strip paper present on the attachment adhesive located on the flaps. EP 0 347 319 B1 to Marsot and WO 88/04546 to Ternstrom disclose the use of a single release paper in the form of a bridging strip across the flap adhesive patches for maintaining the flaps in the folded disposition prior to the wearer's first use of the sanitary napkin.

Two additional examples of this technique are shown in U.S. Pat. No. 5,800,654, to Davis et al. and U.S. Pat. No. 5,662,639 to Tanaka et al. In these methods the attachment adhesive on the flaps is applied in a conventional manner, i.e. via a transfer coating method and a single sheet of release paper acts both as a protective peel strip for the adhesively coated flaps and as a means to hold the flaps in their folded position.

Use of these methods has several drawbacks. These methods require accurate placement of additional adhesives and materials. In particular in the situation in which the flaps are folded onto the body-faceable side of the napkin, adhesives should not come in direct contact with the absorbent material of the sanitary napkin as doing so both adversely effects the absorbency of that material and results in dissatisfaction of the user as to the articles appearance and comfort in use.

Further, use of an additional strip to hold the flaps in their folded position requires additional expense for material at the time of construction and presents an inconvenience to the user in having to discard this material at the time of use. In addition, this method requires that the flaps be maintained in a substantially parallel position relative to one another. If one or both flaps become skewed during manufacture, the adhesive will not be correctly placed on one or both of the flaps, thus rendering it useless. One method of overcoming this problem is to make the peel strip quite large to accommodate this potential skewing, thus exacerbating the problems associated with cost and disposal of peel strip material.

SUMMARY OF THE INVENTION

Accordingly, it is an object of this invention to overcome certain problems of the prior art. Particularly, it is an object of this invention to provide a means to mechanically maintain the flaps in their folded position during manufacturing and to do so without the necessity of additional adhesives or materials.

In accordance with the present invention, there has been provided a novel apparatus for folding a web of flap material over the main body of a sanitary napkin. This apparatus comprises a conveyor means having a substantially fixed velocity for transporting the sanitary napkin, which napkin having a web of laterally extending flap material; a flap folding station for folding said flap material onto said main body of said sanitary napkin; an indexing means comprising a pair of spaced apart finger timing belts, each having a lug affixed thereto, and a finger means intermediate said lugs, said finger means having two ends, each end being mounted onto a respective lug, said finger timing belt imparting a varying velocity to said finger means and establishing repeatable linear and non-linear relationships between the velocities of said finger means and said conveyor means; a napkin folding station for folding said sanitary napkin such that upon completion of the folding, a transverse end portion of said sanitary napkin overlies said web of flap material; wherein: said finger means is adapted to contact and maintain said web of flap material on said main body of said sanitary napkin from said flap folding station to said napkin folding station and, wherein upon completion of the folding of said sanitary napkin by said napkin folding station, said finger means has a velocity less than the velocity of said conveyer means whereby said finger means and said napkin no longer contact one another.

Also provided in accordance with the present invention is a novel method of folding a web of flap material in a continuous manufacturing operation for making absorbent articles, comprising the steps of transporting sanitary napkins along a conveyor means, each napkin having a web of laterally extending flap material; folding said flap material onto said main body of said sanitary napkin; providing an indexing means having a pair of spaced apart finger timing belts, each having at least one lug affixed thereto, each said lug on one timing belt having a counterpart lug on said second timing belt, a finger means intermediate said counterpart lugs, said finger means having two ends, each end being mounted onto a respective lug and thereby resulting in the finger means being substantially orthogonal to both timing belts, said finger timing belts imparting a varying velocity to said finger means and establishing repeatable linear and non-linear relationships between the velocities of said finger means and said conveyor means; folding said sanitary napkin such that upon completion of the folding, a transverse end portion of said sanitary napkin overlies said web of flap material; contacting said finger means with the sanitary napkin to thereby hold said web of flap material on said main body of said sanitary napkin between said steps of folding the flap material and folding the sanitary napkin; and, removing said finger means from contact with said sanitary napkin upon completion of said step of folding of said sanitary napkin.

DETAILED DESCRIPTION OF THE INVENTION

Further characteristics and advantages of the invention will become clear from the following detailed description, appended drawings, and non-limiting examples.

Figure 1:
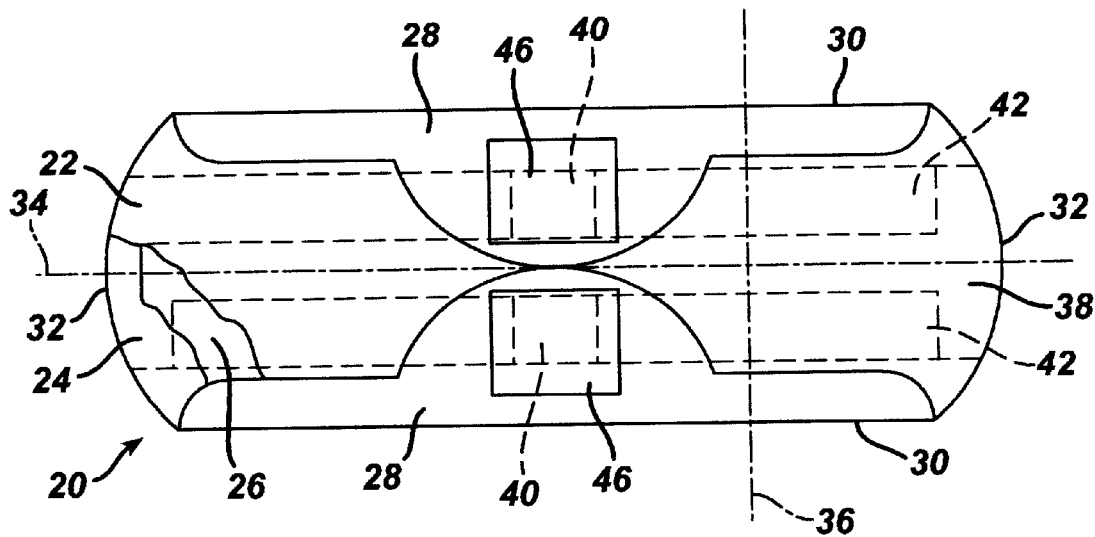
FIG. 1 is a perspective view showing a sanitary napkin of a type that can be folded according to the method and apparatus of the present invention, shown with it flaps in a folded position.

The invention comprises a method and apparatus for folding and retaining the flaps of a sanitary napkin in their folded position. A typical such sanitary napkin is depicted in FIG. 1. The sanitary napkin 20 is adapted to be worn in a user's undergarment and used to collect vaginal discharges, such as menses, and prevent soiling of the wearer's clothing by such discharges. The sanitary napkin 20 features a liquid pervious topsheet 22, a liquid impervious backsheet 24, and an absorbent core 26 intermediate the topsheet 22 and the backsheet 24. As further illustrated in FIG. 1 two flaps 28 extend from transversely opposite side edges 30 of the main body of the sanitary napkin. These flaps are adapted to be folded over a crotch portion of the user's undergarment.

Associated with the sanitary napkin 20 is a means, such as adhesive, for releasably affixing the sanitary napkin 20 to the undergarment of a wearer. In particular, such napkins typically have one or more adhesive areas 42 located substantially in the central region of the garment facing side of the liquid impervious backsheet 24. Further, as depicted in FIG. 1, each flap 28 has an adhesive zone 40. Preferentially, each such adhesive zone is associated with the face of the flap which contacts the undergarment of the wearer. Further, each such adhesive zone 40 is covered by a release strip 46.

In FIG. 1 the flaps are depicted as being folded back onto the topsheet 22, the body-faceable side of the napkin, prior to use. This configuration is preferred by most users as it facilitates removal of release strips 46 and proper placement of the flap adhesive onto the wearer's undergarments.

As is well known in the art, construction of the napkin occurs as the individual napkins move along a conveyor. These individual napkins have a pitch corresponding to the longitudinal dimension of the sanitary napkin. That is, as herein "pitch" refers to the longitudinal distance between corresponding points of adjacent sanitary napkins 20 as they are transported on the conveyor means.

In the preferred embodiment of the present invention, the napkins are fed into the wrapper/folder system from below by means of a vacuum means for temporarily holding the sanitary napkins 20 to the underside of the conveyor. In this configuration, the flaps 28 of the sanitary napkins 20 may be downwardly folded over the topsheets 22 so that the faces of the flaps 28 generally coextensive of the backsheet 24 are exposed and are facing downward as the napkin enters the napkin folding mechanism.

Figure 2:
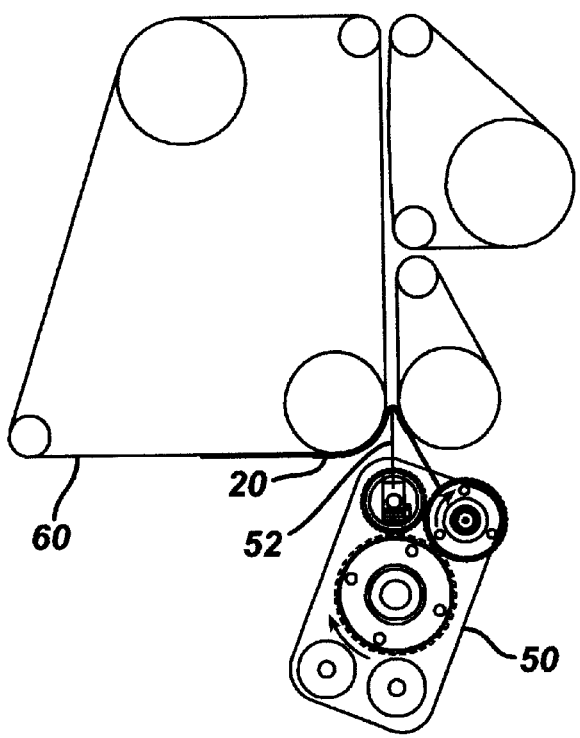
FIG. 2 is a prior art top plan view of a pad folding mechanism.

In the preferred embodiment of the present invention, the folding operation of the napkin utilizes a tucker blade means. Use of such a folding means is well known in the art and is disclosed, for example in U.S. Pat. No. 5,176,615 to Munsch. FIG. 2 illustrates such a napkin folding means 50 which is depicted as employing a tucker blade 52 to initiate folding of a sanitary napkin 20 as the napkin moves along a conveyor means 60.

Not depicted in FIG. 2 is the presence of folded flaps on the underside of the napkin as it enters the napkin folding means. Typically, the presence of flaps folded in this position requires that a tab must be glued onto the flaps prior to the napkin folding process to prevent them from opening and/or skewing. While this problem is more pronounced with flaps on the underside of the napkin, it should be noted that due to the velocity of the napkin along the conveyor, flap opening/skewing can occur even if the manufacturing process is such that the flaps are aided by gravity in being held in there folded position (e.g., when the napkin is on top of the conveyor and the flaps are folded onto the topside of the napkin). The present invention, is applicable to either relative position of the flaps and as noted above, by holding the flaps in their folded position, removes the need for a tab material to be used.

Figure 3:
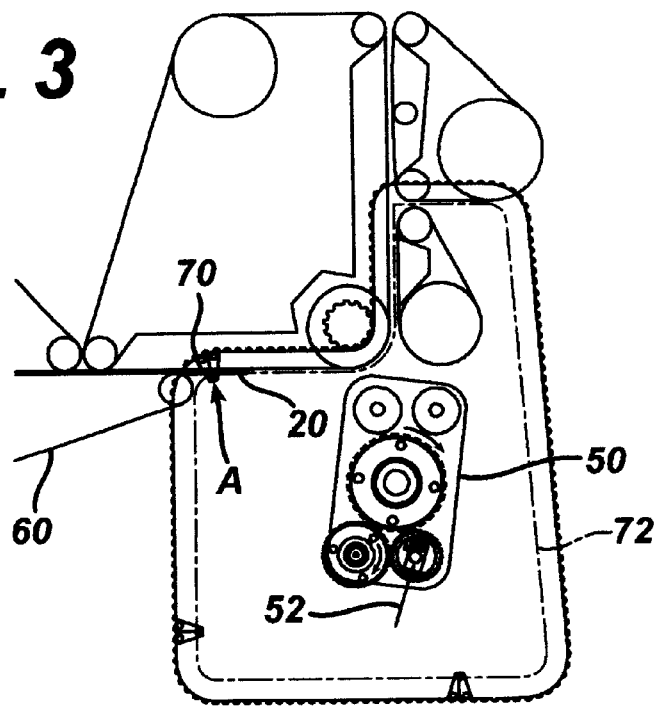
FIGS. 3–6 are top plan views of the present invention depicting the finger means path relative to the position of a napkin on the conveyor and the corresponding tucker blade positions.

As depicted in FIG. 3 the preferred embodiment of the present invention utilizes one or more finger means 70 which transverses a finger path 72 which forms a continuous loop path about the napkin folding means 50. The length of the finger path is determined such that in the event there is only one finger; it will traverse the finger path in the pitch period of the napkins 20 as they travel along the conveyor. In the preferred embodiment of the invention two or more fingers are present and the length of the finger path is such that as successive napkins approach the napkin folding means, a finger makes contact with the flaps of the napkin at substantially the same finger contact point "A" along the conveyor path. The ability to time such a mechanical operation relative to the pitch period is well known in the prior art.

This contact point "A" occurs at a position along the conveyor means after the flaps of the napkin have been folded to the underside of the napkin. Such folding of the flaps is well known in the prior art and is taught, for example, by U.S. Pat. No. 5,714,027 issued to Taub.

In the preferred embodiment of the present invention and as further depicted in FIG. 3, this finger contact point occurs shortly after the conveyor used to support the underside of the napkin turns downward and the napkin then lies beneath and is transported by a subsequent conveyor mechanism which utilizes a vacuum force to support the napkin.

Figure 4:
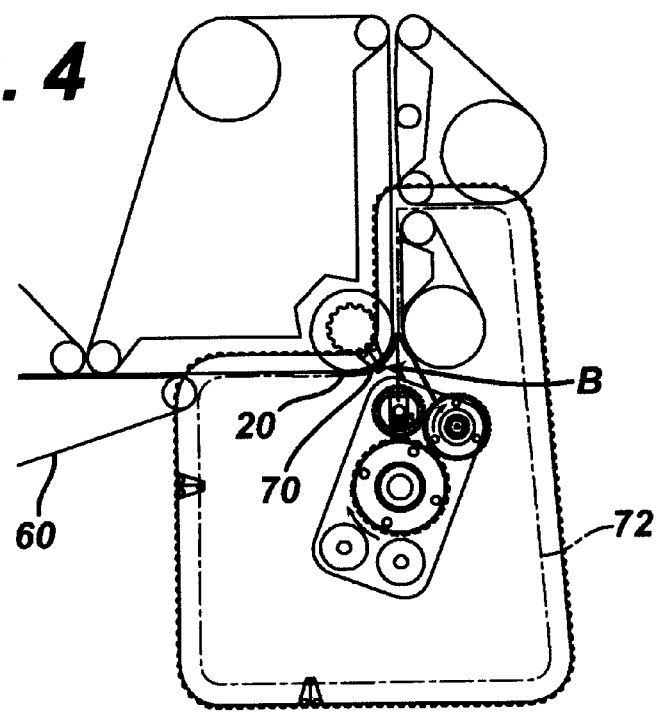

As depicted in FIG. 4, the finger means 70 then continues along the finger path thereby remaining substantially parallel to the conveyor means 60 as the napkin 20 moves from position "A" to the point at which the tucker blade makes contact with the napkin, point "B". As it traverses this distance the flaps of the napkin are held in their folded position by the finger means.

Figure 5:
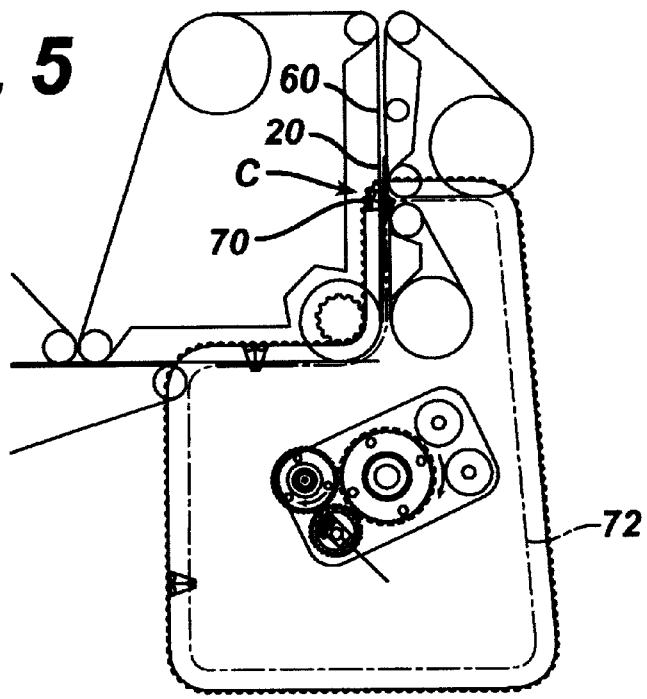

In the preferred embodiment of the invention, and as depicted in FIG. 5, the finger means 70 remains in contact with the napkin 20 until the napkin has been folded—depicted at position C. By way of example and as depicted in FIG. 1, a transverse end portion 38 of the napkin would be folded along fold line 36 thereby overlaying the folded flaps of the napkin and consequently holding the flaps in their folded positions.

Figure 6:
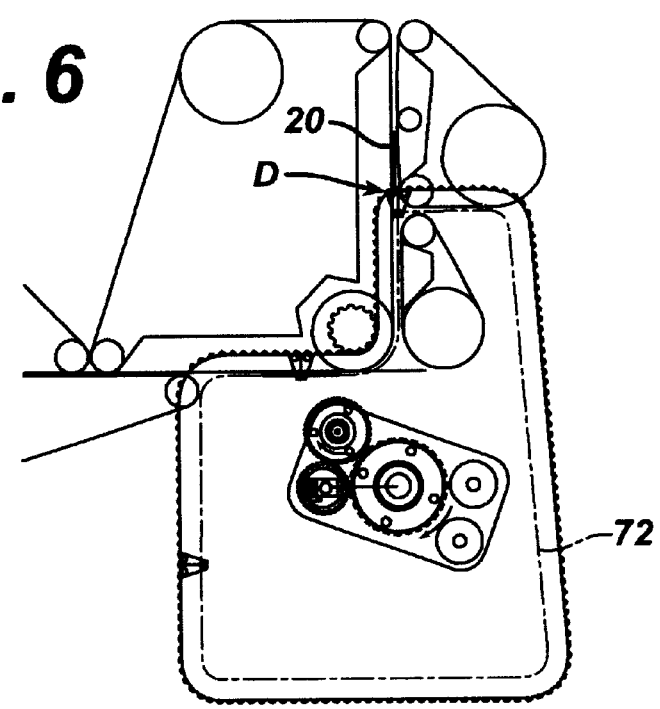

As indicated further in FIG. 5, at this point, "C", the finger path ceases to run substantially parallel to the conveyor means. Moreover, as depicted in FIG. 6 at point "D", the finger means reduces its simultaneous direction of travel with the napkin 20 thereby permitting the folded napkin to continue along the conveyor means for subsequent processing without the finger means being in contact with the napkin. Such subsequent processing may include, but not be limited to, additional folding and packaging operations.

Figure 7:
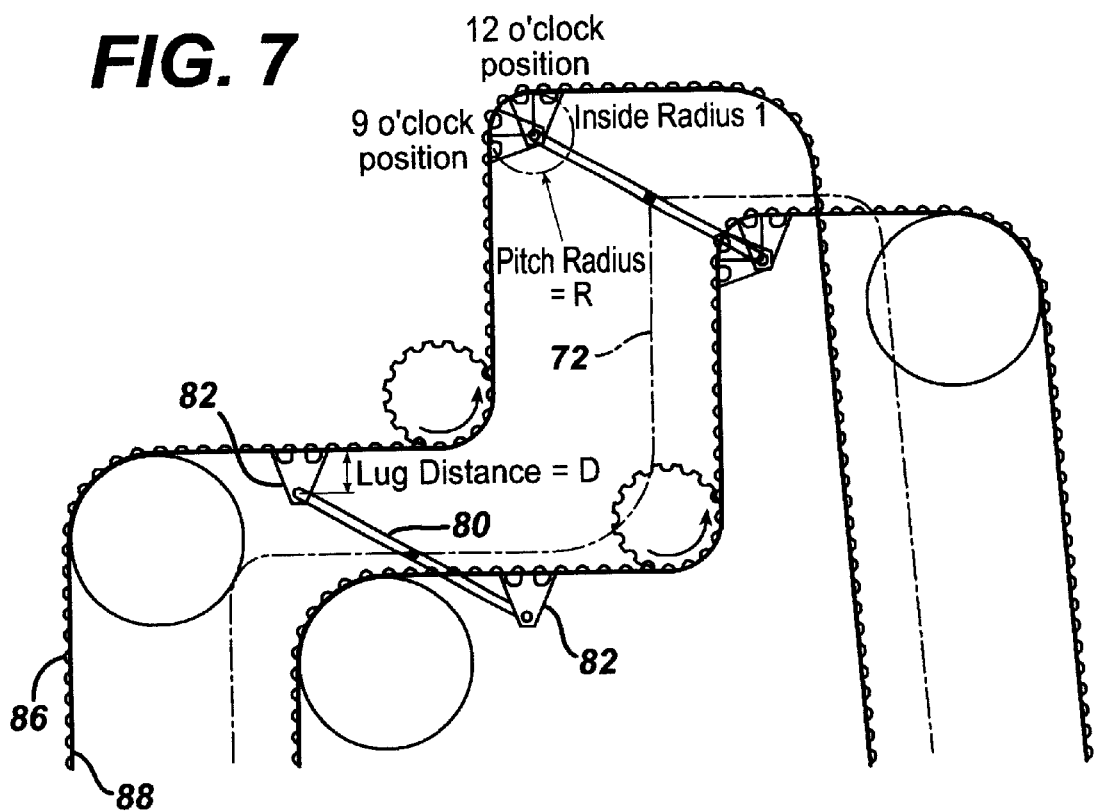
FIG. 7 is a three dimensional partial view of the finger means and associated components of the present invention.

As depicted in FIG. 7, the finger means comprises two parallel timing belts, each having at least one lug 82, said lugs being arranged in pairs between the timing belts. A finger means rod 80 is mounted between associated pairs of said lugs. Each timing belt forms a continuous loop with a pitch length that is a multiple of the distance between rods. In this manner the position of the finger means rod is always at the same spot after each cycle.

Figure 8:
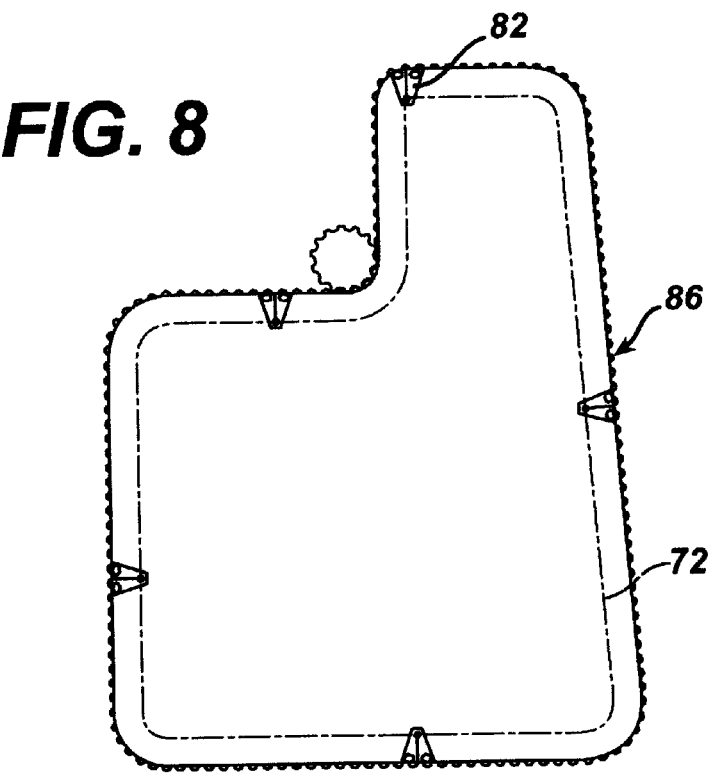
FIG. 8 is a top plan view of the finger path of the present invention.

As noted above, and as depicted in FIGS. 3, 6 and 8, the finger means path 72 is designed so that the finger means travels the same path as the napkin from the time when it enters into the napkin folding process (position A of FIG. 3) until it exits the folder (position D of FIG. 6). As the belt traverses about its designed path, it makes inside and outside turns to form the continuous loop.

As is well known in the art, the motion of the finger means relative to the conveyor means can be mathematically determined. This analysis begins with defining the pitch line 88 to be the geometric center of the timing belt 86. As indicated in FIG. 7, maintaining the perpendicular distance or lug distance, D, of the finger rod 80 to the pitch line 88 equal to the pitch radius, R, of an inside turn (i.e. D=R), results in the finger dwelling at that inside radius with a duration equal to the wrap angle, where the wrap angle is the length of the arc defined by the finger timing belts contact with a sprocket or pulley. The amount of dwell will be proportional to the wrap angle. Moreover, if the wrap angle is 90 degrees, the finger will make a right angle turn.

The operation of this dwelling mechanism in the preferred embodiment of the present invention is depicted in FIG. 7. The finger means lug is at a 9 o'clock position as it arrives at the point "D" depicted in FIG. 6. As the lug then traverses from this 9 o'clock to a 12 o'clock position, the finger remains stationary. The finger path then travels in a direction perpendicular to and away from the napkin conveyor. Consequently, this dwelling and right angle motion results in the finger means discontinuing contact with the napkin as the napkin continues along the conveyor subsequent to position D.

The specification and embodiments above are presented to aid in the complete and non-limiting understanding of the invention disclosed herein. Since many variations and embodiments of the invention can be made without departing from its spirit and scope, the invention resides in the claims hereinafter appended.

I claim:

1. A method of folding a web of flap material to overlay the main body of an absorbent article in a continuous manufacturing operation for making said absorbent articles, said method comprising the steps of:

transporting successive sanitary napkins along a conveyor means, each napkin having a web of laterally extending flap material;

folding said flap material onto said main body of said sanitary napkin;

providing an indexing means having a pair of spaced apart finger timing belts, each having a lug affixed thereto, and a finger means intermediate said lugs, said finger means having two ends, each end being mounted onto a respective lug, said finger timing belt imparting a varying velocity to said finger means and establishing repeatable linear and non-linear relationships between the velocities of said finger means and said conveyor means;

folding said sanitary napkin such that upon completion of the folding, a transverse end portion of said sanitary napkin overlies said web of flap material;

contacting said finger means with the sanitary napkin to thereby hold said web of flap material onto said main body of said sanitary napkin between said steps of folding the flap material and folding the sanitary napkin; and, removing said finger means from contact with said sanitary napkin upon completion of said step of folding of said sanitary napkin.

2. The method of claim 1 wherein the step of removing said finger means comprises the step of reducing the velocity of said finger means to a velocity less than that of said conveyor means.

3. The method of claim 2 wherein said step of folding said sanitary napkin comprises utilizing a tucker blade means.

4. The method of claim 3 wherein said folding step further comprises folding said flap material onto said body-faceable side of said main body of said sanitary napkin.

5. An apparatus for folding a web of flap material to overlay the main body of a sanitary napkin, said apparatus comprising:

a conveyor means having a substantially fixed velocity for transporting said sanitary napkin, said napkin having a web of laterally extending flap material;

a flap folding station for folding said flap material onto said main body of said sanitary napkin;

an indexing means comprising a pair of spaced apart finger timing belts, each having a lug affixed thereto, and a finger means intermediate said lugs, said finger means having two ends, each end being mounted onto a respective lug, said finger timing belts imparting a varying velocity to said finger means and establishing repeatable linear and non-linear relationships between the velocities of said finger means and said conveyor means;

a napkin folding station for folding said sanitary napkin such that upon completion of the folding, a transverse end portion of said sanitary napkin overlies said web of flap material;

wherein said finger means is adapted to contact and maintain said web of flap material on said main body of said sanitary napkin from said flap folding station to said napkin folding station; and, wherein upon completion of the folding of said sanitary napkin by said napkin folding station, said finger means has a velocity less than the velocity of said conveyer means whereby said finger means and said napkin no longer contact one another.

6. A flap folding apparatus as recited in claim 5 wherein said indexing means has a plurality of said finger means.

7. A flap folding apparatus as recited in claim 6 wherein the movement of each said finger means comprises a first interval during which each said finger means moves substantially parallel to and at the same velocity as the conveyor means, a second interval during which each said finger means dwells, and a third interval during which each said finger means moves in a direction away from the conveyor means.

8. A flap folding apparatus as recited in claim 7 wherein said napkin folding station comprises a tucker blade means.

9. A flap folding apparatus as recited in claim 8 wherein said indexing means comprises a finger timing belt, said finger timing belt forming a continuous loop about said tucker blade means, and wherein said continuous loop defines a finger means path.

10. A flap folding apparatus as recited in claim 9 wherein said conveyor means transports a plurality of sanitary napkins, said conveyor means having a pitch wherein corresponding points of adjacent sanitary napkins have a substantially fixed longitudinal distance; and wherein said continuous loop completes a cyclical revolution that is a multiple of the pitch and wherein each said finger means is at the same spot after each cycle.

11. A flap folding apparatus as recited in claim 10 wherein said finger means path causes the finger means to substantially travel the same path as the conveyor means from the time when the sanitary pad enters into said napkin folding station until it exits said station.

12. A flap folding apparatus as recited in claim 11 wherein said flap folding station folds said flap material onto the body-faceable side of said main body of said sanitary napkin.

13. A flap folding apparatus as recited in claim 1 wherein said repeatable linear and non-linear relationships between the velocities of said finger means and said conveyor means are at least partially established by predetermined angular positions of said lug with respect to its corresponding finger timing belt.

* * * * *